United States Patent
Sung et al.

(10) Patent No.: US 9,539,326 B2
(45) Date of Patent: Jan. 10, 2017

(54) ACID-SUBSTITUTED POLYANILINE-GRAFTED HYDROGEL COPOLYMER AND USE THEREOF

(71) Applicant: National Tsing Hua university, Hsinchu (TW)

(72) Inventors: Hsing-Wen Sung, Hsinchu (TW); Chun-Wen Hsiao, Hsinchu (TW); Chieh-Cheng Huang, Hsinchu (TW); Min-Fan Chung, Hsinchu (TW); Zi-Xian Liao, Kaohsiung (TW); Wei-Lun Chiang, Hsinchu (TW)

(73) Assignee: NATIONAL TSING HUA UNIVERSITY, Hsinchu (TW)

(*) Notice: Subject to any disclaimer, the term of this patent is extended or adjusted under 35 U.S.C. 154(b) by 0 days.

(21) Appl. No.: 15/170,257

(22) Filed: Jun. 1, 2016

(65) Prior Publication Data

US 2016/0271250 A1 Sep. 22, 2016

Related U.S. Application Data

(63) Continuation-in-part of application No. 14/488,571, filed on Sep. 17, 2014, now abandoned.

(30) Foreign Application Priority Data

Jul. 2, 2014 (TW) .............................. 103122880 A

(51) Int. Cl.

| | |
|---|---|
| A61K 41/00 | (2006.01) |
| C08G 73/02 | (2006.01) |
| C08G 81/00 | (2006.01) |
| C08B 37/08 | (2006.01) |
| A61K 47/48 | (2006.01) |
| A61N 5/06 | (2006.01) |
| C08J 3/075 | (2006.01) |
| C08L 5/08 | (2006.01) |

(52) U.S. Cl.
CPC ..... *A61K 41/0052* (2013.01); *A61K 47/48192* (2013.01); *A61K 47/48784* (2013.01); *A61N 5/062* (2013.01); *A61N 5/0624* (2013.01); *A61N 5/0625* (2013.01); *C08B 37/003* (2013.01); *C08G 73/0266* (2013.01); *C08G 81/00* (2013.01); *C08J 3/075* (2013.01); *C08L 5/08* (2013.01); *A61N 2005/0659* (2013.01); *C08J 2351/02* (2013.01)

(58) Field of Classification Search
None
See application file for complete search history.

(56) References Cited

U.S. PATENT DOCUMENTS 7,273,918 B2 * 9/2007 Han ..................... C08G 61/122
528/210

OTHER PUBLICATIONS

Marcasuzaa, P., et al. "Chitosan-graft-polyaniline-based hydrogels: elaboration and properties." Biomacromolecules 11.6 (2010): 1684-1691.*

Yang, Jaemoon, et al. "Convertible Organic Nanoparticles for Near-Infrared Photothermal Ablation of Cancer Cells." Angewandte Chemie International Edition 50.2 (2011): 441-444.*

* cited by examiner

*Primary Examiner* — Bethany Barham
*Assistant Examiner* — Peter Anthopolos
(74) *Attorney, Agent, or Firm* — Li & Cai Intellectual Property (USA) Office

(57) ABSTRACT

An (acid-substituted polyaniline)-grafted hydrogel copolymer is provided. The (acid-substituted polyaniline)-grafted hydrogel copolymer has a general formula as below:

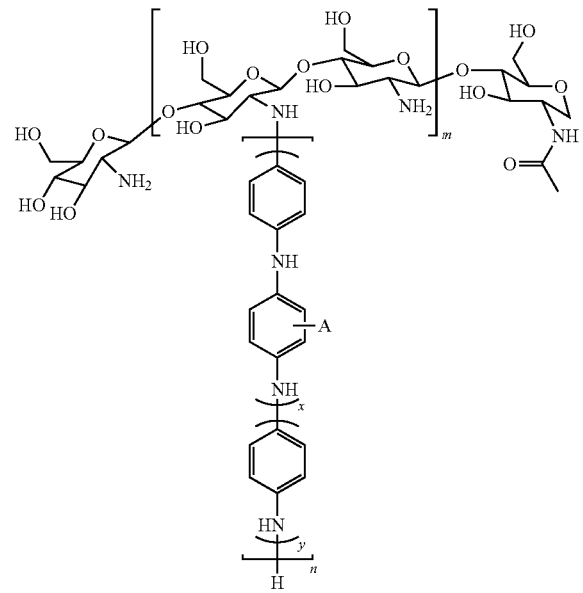

wherein A is a proton acid group, m and n are same or different integers greater than 0, x is an integer equal to or greater than 0, and y is an integer equal to or greater than 1, provided that x and y are the same or different at each occurrence, and at least an x is not 0. The (acid-substituted polyaniline)-grafted hydrogel copolymer is formed by the polymerization and substitution reaction between chitosan, polyaniline, and proton acid. The (acid-substituted polyaniline)-grafted hydrogel copolymer behaves as a pH-responsive hydrogel with photo-thermal properties and can be applied to photo-thermal therapy.

14 Claims, 18 Drawing Sheets
(11 of 18 Drawing Sheet(s) Filed in Color)

FIG. 11A                    FIG. 11B

ACID-SUBSTITUTED POLYANILINE-GRAFTED HYDROGEL COPOLYMER AND USE THEREOF

CROSS REFERENCE TO RELATED APPLICATION

This application is a continuation-in-part of U.S. application Ser. No. 14/488,571 filed on Sep. 17, 2014 and entitled "ACID-SUBSTITUTED POLYANILINE-GRAFTED HYDROGEL COPOLYMER AND USE THEREOF", now pending, the entire disclosures of which are incorporated herein by reference.

BACKGROUND OF THE INVENTION

1. Field of the Invention

The instant disclosure relates to a hydrogel copolymer and the use thereof; in particular, to an (acid-substituted polyaniline)-grafted hydrogel copolymer and the use thereof.

2. Description of Related Art

Recently, photo-thermal therapy is used to treat cancers or subcutaneous tissue/skin diseases caused by bacteria. The therapy uses a photo-thermal agent to absorb a light with specific wavelength and generate heat energy that can increase the temperature of the tissue to affect the viability of bacteria/cancer cells. For example, the photo-thermal agent can absorb Near-Infrared (NIR) light and convert it into heat energy to increase the temperature of the infection potion. While the temperature of the infection potion is higher than 50° C., bacteria/cancer cells are damaged, eventually leading to their death.

The common photo-thermal agent is the metal exhibiting proper photo-thermal features, such as Au, Ag, Pb, and Ge. The metal has a strong absorption in the NIR wavelength region (750 to 1000 nm) In general, the metal has stable absorption only when it maintains particular shape. Take Au for example, can have stable absorption in the NIR wavelength region while it maintains its shape such as shell-type, cylindrical, or cubic. Nevertheless, the above-mentioned shape might be damaged and destroyed under long-term exposure to NIR. Thus, the absorption of the photo-thermal agent in the NIR wavelength region and the photo-thermal conversion efficiency might decrease.

SUMMARY OF THE INVENTION

The instant disclosure provides an (acid-substituted polyaniline)-grafted hydrogel copolymer, which has stable photo-thermal conversion efficiency.

The instant disclosure provides a use of an (acid-substituted polyaniline)-grafted hydrogel copolymer, which is used in photo-thermal therapy.

The instant disclosure provides an (acid-substituted polyaniline)-grafted hydrogel copolymer. The hydrogel copolymer is formed by the polymerization and substitution reaction between chitosan, polyaniline, and proton acid. The hydrogel copolymer has a general formula as below:

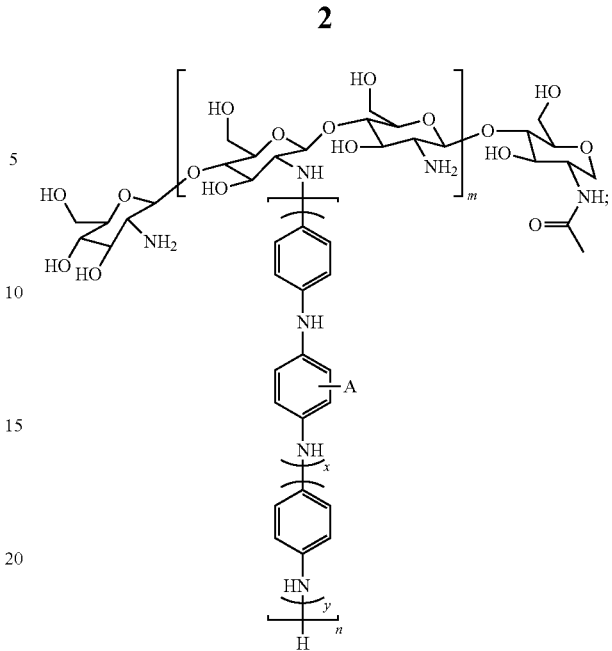

wherein A is a proton acid group, m and n are same or different integers greater than 0, x is an integer equal to or greater than 0, and y is an integer equal to or greater than 1, provided that x and y are the same or different at each occurrence, and at least an x is not 0. The hydrogel copolymer can behave as a pH-responsive hydrogel with photo-thermal properties and can be applied to the photo-thermal therapy.

In summary, the instant disclosure provides the (acid-substituted polyaniline)-grafted hydrogel copolymer. The hydrogel copolymer is formed by the polymerization and substitution reaction between chitosan, polyaniline, and proton acid. The chitosan group makes the copolymer be transformed into hydrogels in a process that is driven by a local change in pH. The polyaniline group grafted by the acid proton group makes the hydrogel copolymer have an absorption in the NIR wavelength region. The acid proton group makes the polyaniline group maintain itself in the doped form.

In order to further understand the instant disclosure, the following embodiments and illustrations are provided. However, the detailed description and drawings are merely illustrative of the disclosure, rather than limiting the scope being defined by the appended claims and equivalents thereof.

BRIEF DESCRIPTION OF THE DRAWINGS

The patent or application file contains at least one drawing executed in color. Copies of this patent or patent application publication with color drawings will be provided by the Office upon request and payment of necessary fee.

FIG. 11A to 11C are the Histological H&E stain photomicrographs of the skin tissue section of infected mice before and after NMPA-CS and laser treatment in accordance with the embodiment of the instant disclosure;

DETAILED DESCRIPTION OF THE PREFERRED EMBODIMENTS

Figure 1:
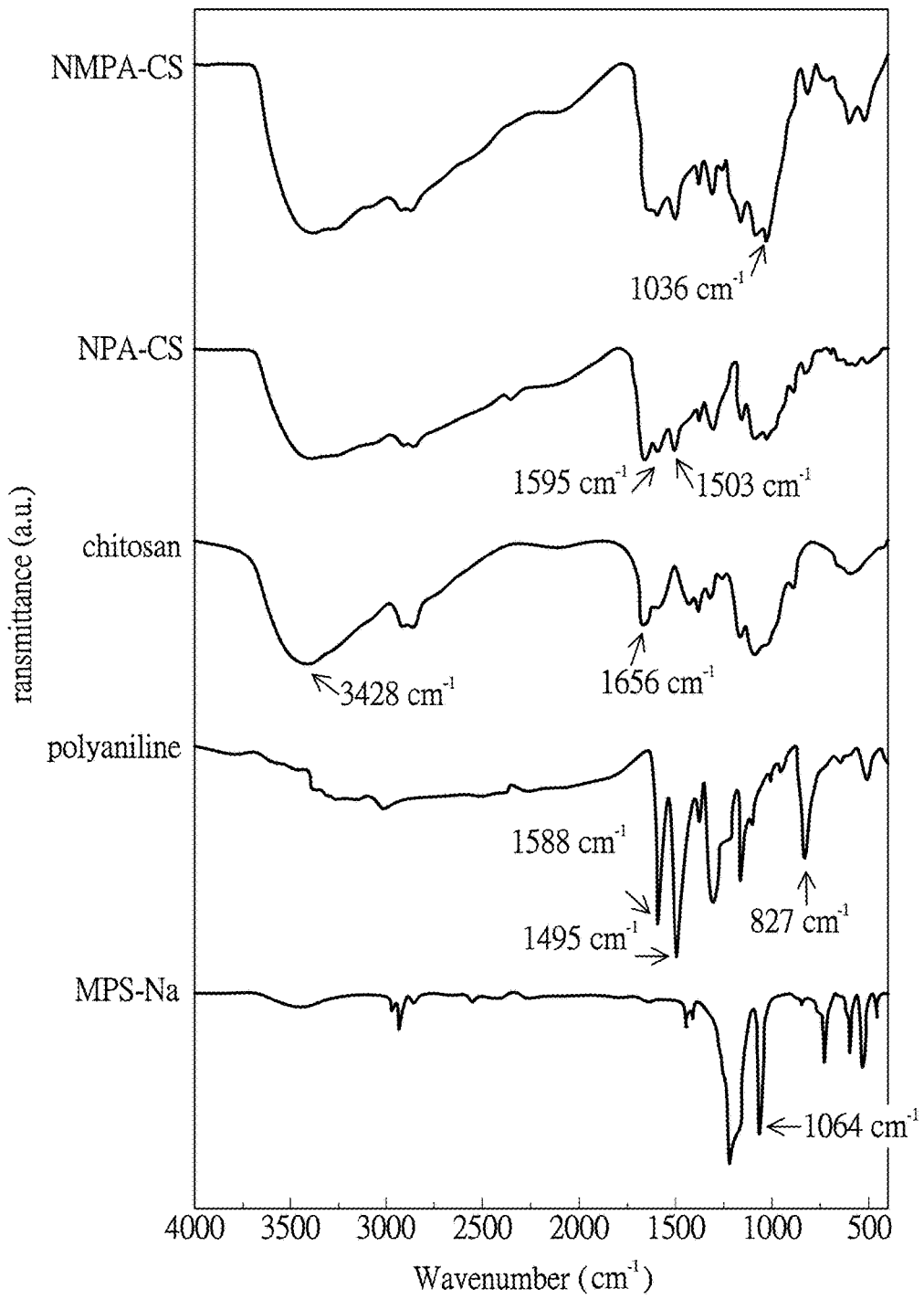
FIG. 1 shows the FT-IR spectra of chitosan (CS), polyaniline (PANI), MPS-Na, NPA-CS, and NMPA-CS in accordance with an embodiment of the instant disclosure.

The instant disclosure provides an (acid-substituted polyaniline)-grafted hydrogel copolymer. The hydrogel copolymer is formed by the polymerization and substitution reaction between chitosan, polyaniline, and proton acid. The hydrogel copolymer comprises a chitosan group, a polyaniline group, and a proton acid group. The general formula of polyaniline-grafted hydrogel copolymer is shown as below:

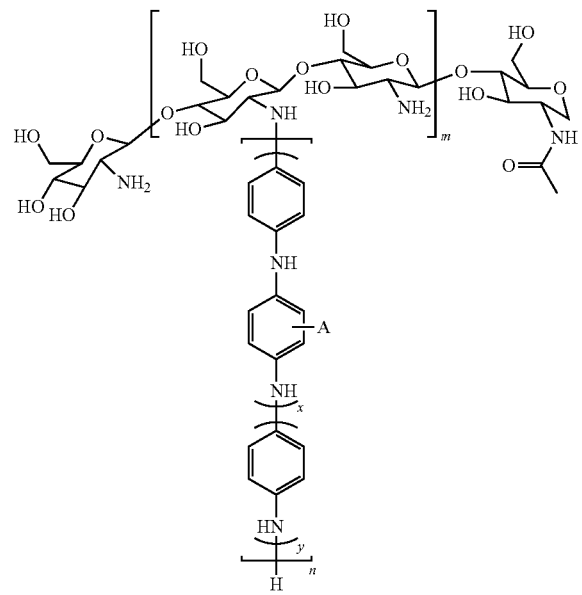

wherein A is a proton acid group, m and n are same or different integers greater than 0, x is an integer equal to or greater than 0, and y is an integer equal to or greater than 1, provided that x and y are the same or different at each occurrence, and at least an x is not 0. To be specific, when n is equal or greater than 2 (n is not 1), x and y are the same or different at each occurrence, and at least an x is not 0, i.e., the aniline group with the proton acid group should be always existed in the general formula.

The proton acid group is selected from the group consisting of: 3-mercapto-1-propanesulfonic acid sodium salt (MPS-Na), 3-mercaropropinoic acid, and thioglycolic acid. In the present embodiment, MPS-Na is taken as the proton acid group, and the MPS-Na substituted polyaniline-grafted hydrogel copolymer is referred as NMPA-CS.

Notably, chitosan is a biodegradable and tissue compatible material. In addition, chitosan is a pH-responsive hydrogel. The chitosan is presented as viscous liquid in the environment at pH between 6.0-6.5. In contrast, while the chitosan is brought into physiological environment (pH 7.0-7.4), it is presented as hydrogels. Polyaniline is considered as a non-cytotoxic material with highly environmental stability and has been applied in various biomedical applications. Polyaniline is one of the best characterized conducting polymers. Specifically, in an environment with the highly proton concentration, polyaniline is doped by a proton to stay in the conductive state and its optical-absorbance peak is red-shifted toward the NIR region. Therefore, polyaniline can absorb the NIR light and generate a substantial amount of heat energy that can be used in the photo-thermal therapy. In other words, polyaniline can absorb the NIR light at the acidic condition.

However, in the environment without high proton concentration, such as the physiological pH environment or neutral pH environment (pH=7.0 to 7.4), polyaniline stays in the deprotonation state. Thus, the polyanilne loses its NIR photo-thermal activity. In the embodiment of the instant disclosure, the polyaniline of the NMPA-CS can be self-doped by the MPS in the physiological pH environment or neutral pH environment. Thus, the polyaniline can stay in the doped form and absorb the NIR light.

In the photo-thermal therapy, the photo-thermal agent is injected at the site of infection or tumor tissue formed by cancer cells. Then, the site of infection or tumor tissue is exposed to the light with specific wavelength to generate a heat energy that can lead to bacteria/tumor tissue death. In practice, the NMPA-CS can be taken as a photo-thermal agent and be applied to the photo-thermal therapy. Since the chitosan of the NMPA-CS has a pH-responsive property, the NMPA-CS can be immobilized at the site of infection. In addition, the NIR light is used to irradiate the site of infection. Due to its low absorbance by tissue chromophores, the NIR light is able to penetrate the skin with a depth up to 10 mm without causing significant damage to blood and healthy tissues. Accordingly, it has been considered as one of the most adequate light sources for photo-thermal therapy that can focus on a targeted area for effective treatment.

The instant disclosure also provides the manufacturing method of the NMPA-CS. It worth noting that, the n in the above-mentioned general formula of NMPA-CS refers to the polymerization degree of the NMPA-CS. However, since the NMPA-CS is formed by the polymerization between hydrophobic polyaniline and hydrophilic chitosan, it is difficult to define the polymerization degree by the Nuclear Magnetic Resonance Spectroscopy or Mass Spectrometry in real practice. Therefore, in the embodiment of the instant disclosure, the polymerization degree is defined by the polymerization time described in the following introduction of the manufacturing method and omitted hereinafter, and the polymerization degree n of the NMPA-CS is in positive correlation with the polymerization time between the polyaniline and the chitosan.

The manufacturing method of the NMPA-CS comprises two main steps: grafting the polyaniline onto the chitosan to form the polyaniline-grafted hydrogel copolymer (referred as NPA-CS) and grafting the MPS-Na onto the NPA-CS to form the (acid-substituted polyaniline)-grafted hydrogel copolymer (NMPA-CS). Firstly, the reaction of grafting the polyaniline onto the chitosan to form the NPA-CS is listed as below:

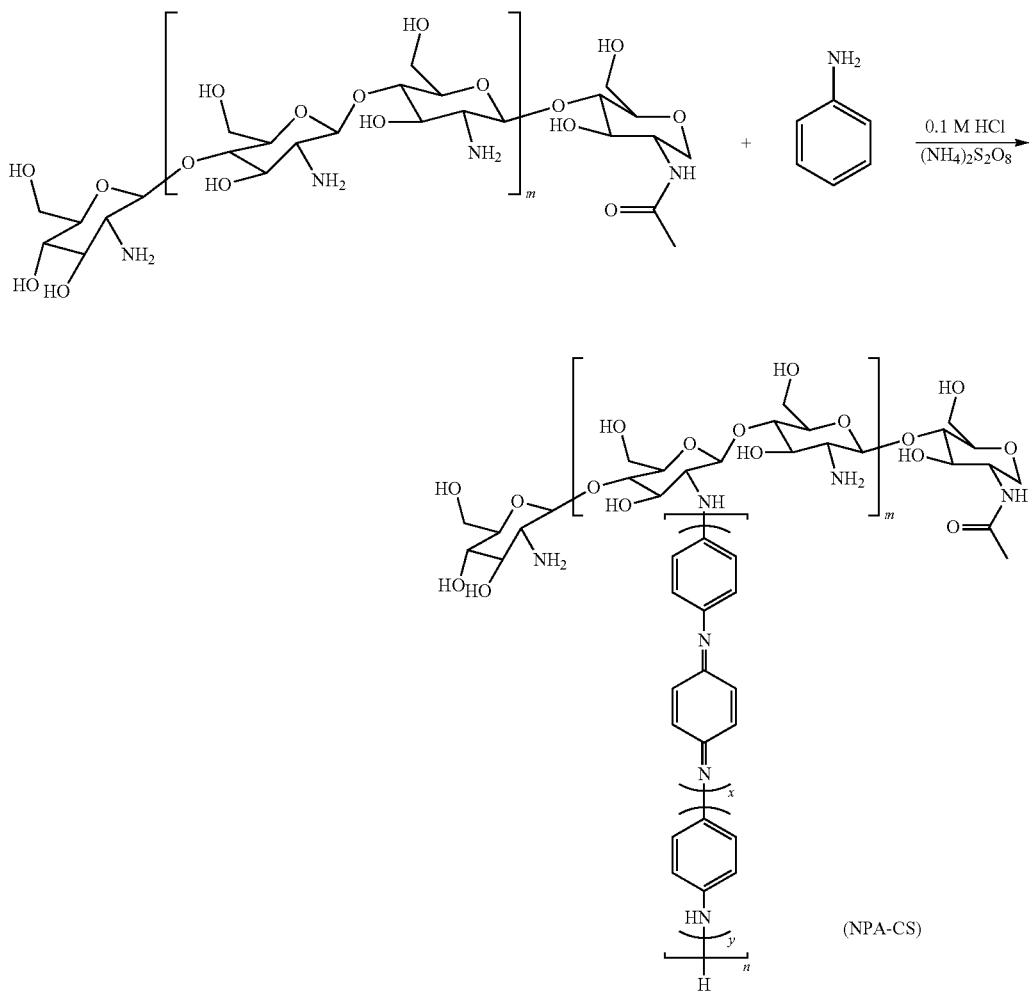

The reaction of grafting the polyaniline onto the chitosan comprises the following steps. Firstly, 2 g of chitosan is added into the 900 ml of hydrochloric acid (0.1 M). An aqueous mixture of chitosan and HCl is stirred overnight to ensure total solubility. Then, 14.5 mM of aniline is subsequently added to the chitosan solution. After solubilization, equimolar of ammonium persulfate is introduced into the mixed solution. The polymerization of polyaniline and chitosan is carried out for 3.5 to 4.5 hours with stirring in an ice bath. It worth noting that, the stirring time in the ice bath is the time for polymerizing the polyaniline and grafting the polyaniline onto the chitosan. In the preferred embodiment, the polymerization and grafting time is about 4 hours.

Next, the as-prepared NPA-CS copolymer is then neutralized and precipitated by adding sodium hydroxide (NaOH) having a pH value of 8.0. After that, free polyaniline is removed with 1-methyl-2-pyrrolidinone (NMP) and NPA-CS is obtained.

The reaction of grafting the MPS-Na onto the NPA-CS to form the NMPA-CS is shown below:

stitution reaction (CRS reaction). The reaction temperature is around room temperature. The CRS time of the reaction is the polymerization time of the MPS-Na grafting onto the NPA-CS. In the preferred embodiment, the polymerization time is about 14 hours. In addition, a catalytic amount of acetic acid (0.01 M) is added to accelerate the reaction. The resultant copolymer, NMPA-CS, is precipitated by NaOH (pH value is 8.0), washed with an excess of DI water, and then air-dried.

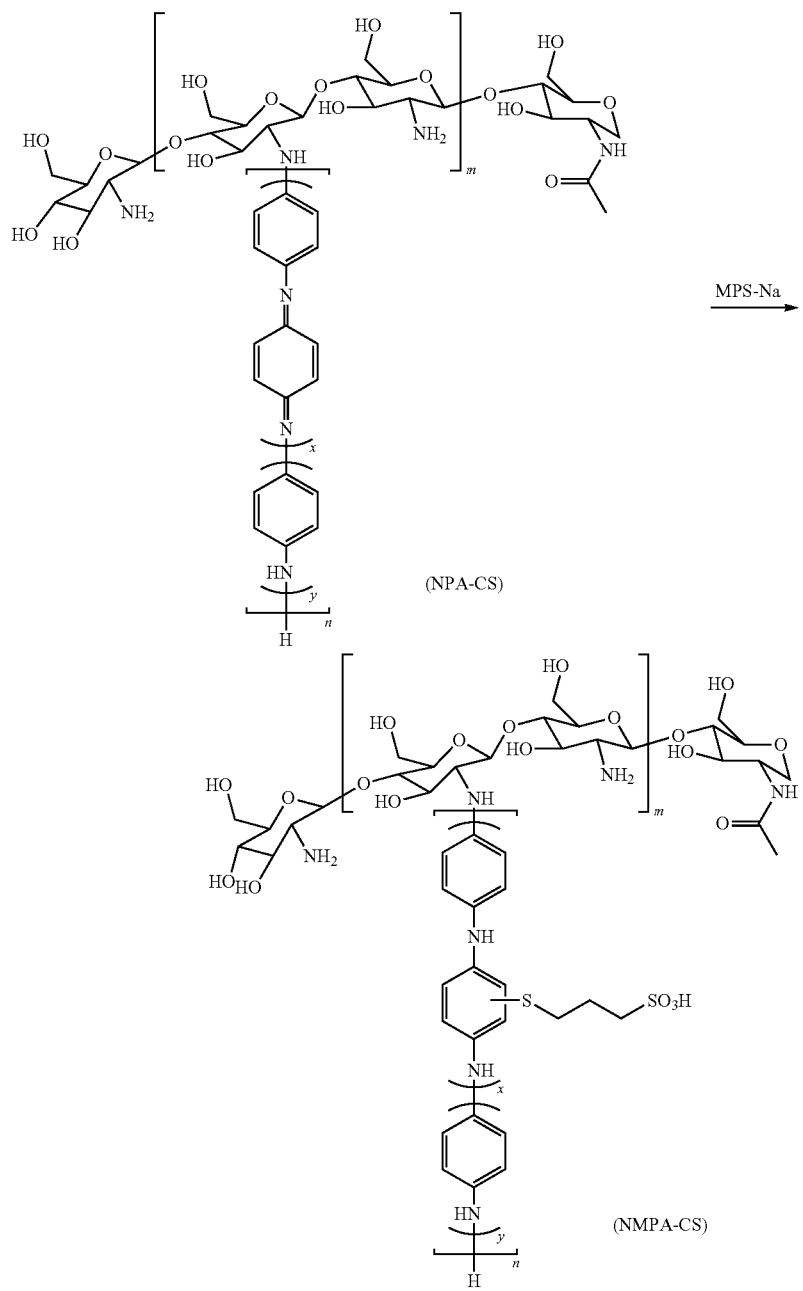

The reaction of grafting the MPS-Na onto the NPA-CS comprises the following steps. Firstly, 1 g of NPA-CS is added into the 0.1 M of the MPS-Na in deionized water (DI water) 150 mL under a $N_2$ atmosphere for 12-16 hours to allow the completion of the concurrent reduction and sub- It worth noting that, the synthesized NMPA-CS and NPA-CS are dissolved into the 1% of acetic acid solution and the mixture solution is stirred until completely dissolving. After that, the NMPA-CS and the NPA-CS solutions are dialyzed by the deionized water. In the present embodiment, the MWCO: 3500 Da of the dialysis bag is used. During the process of the dialysis, the deionized water needs to be replaced until the pH value of the NMPA-CS solution is at the range of 6.0 to 6.2. Then, the NMPA-CS and NPA-CS solution are adjusted to the desired concentration to make the following analysis.

After the NMPA-CS is synthesized, the NMPA-CS is analyzed by FT-IR (Perkin-Elmer, Buckinghamshire, UK) to confirm whether the polyaniline is grafted onto the chitosan and whether the MPA-Na is grafted onto the polyaniline FIG. 1 is a FT-IR spectra of CS, PANI, MPS-Na, NPA-CS, and NMPA-CS in accordance with an embodiment of the instant disclosure. Referring to FIG. 1, the spectrum of MPS-Na shows one characteristic peak at 1064 $cm^{-1}$, representing the S=O stretching. The spectrum of polyaniline shows three characteristic peaks at 1588 $cm^{-1}$, 1495 $cm^{-1}$, and 827 $cm^{-1}$, representing the benzenoid rings, quinoid rings, and C—H stretching vibrations, respectively. In addition, the spectrum of chitosan shows one characteristic peak of N—H at 1656 $cm^{-1}$ and one characteristic peak of —OH at 3428 $cm^{-1}$.

As shown in FIG. 1, both of the FT-IR spectrums of NPA-CS and NMPA-CS show the characteristic peaks of benzenoid rings, quinoid rings, and C—H stretching vibrations (in FIG. 1, since the grafting reaction, the benzenoid rings and quinoid rings are slightly shifted). In addition, both of the spectrums of NPA-CS and NMPA-CS show the characteristic peaks of chitosan at 1656 $cm^{-1}$ and 3428 $cm^{-1}$, representing the N—H and —OH stretching vibrations, respectively. In other words, both the NPA-CS and NMPA-CS have the characteristic peaks of the polyaniline and chitosan. The polyaniline is indeed grafted onto the chitosan in NPA-CS and NMPA-CS. Moreover, the characteristic peak of S=O in NMPA-CS is slightly shifted to 1036 $cm^{-1}$. In other words, MPS-Na is indeed grafted onto the polyaniline in NMPA-CS.

In the following paragraph, the photo-thermal feature, photostability, antibacterial activity, and in vivo/in vitro efficacy of NMPA-CS and NPA-CS are evaluated. The NMPA-CS is taken as an embodiment and the NPA-CS is taken as a comparative example to introduce the application and efficiency of the (acid-substituted polyaniline)-grafted hydrogel copolymer provided in the instant disclosure.

Figure 2A:
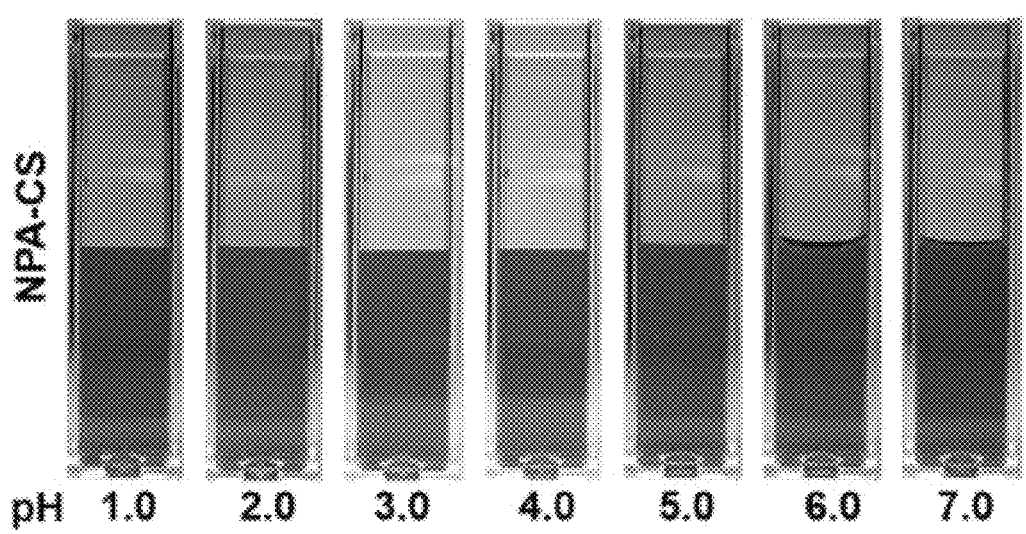
FIG. 2A is a photograph of NPA-CS aqueous solutions in different pH environments in accordance with the embodiment of the instant disclosure.
Figure 2B:
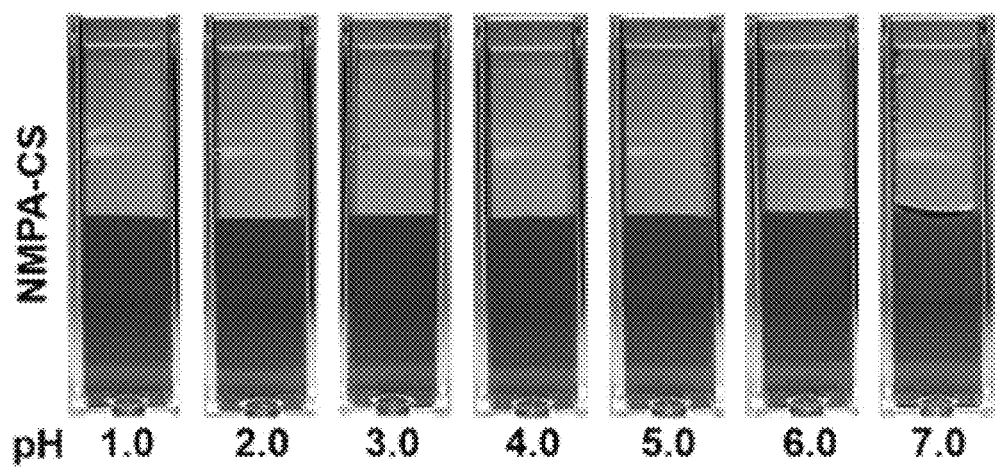
FIG. 2B is a photograph of NMPA-CS aqueous solutions in different pH environments in accordance with the embodiment of the instant disclosure.

Firstly, the variations of the doping types of the NMPA-CS and NPA-CS in different environment pH values are evaluated. In the present embodiment, while the NMPA-CS is in the environment at pH between 1 to 8, the NMPA-CS is in the doping form and has an absorption in the NIR wavelength region. FIG. 2A is a photograph of NPA-CS aqueous solution in different pH value environments in accordance with the embodiment of the instant disclosure and FIG. 2B is a photograph of NMPA-CS aqueous solution in different pH value environments in accordance with the embodiment of the instant disclosure. As shown in FIGS. 2A and 2B, the color of the NMPA-CS remains green, meaning a doping form, in the pH range from 1 to 7. Conversely, the color of the NPA-CS is green only in a strongly acidic environment (pH value ranged from 1 to 3). When the pH environment approaches the physiologic condition (pH value ranged from 4 to 7), the color of the NPA-CS becomes blue, means an undoped form.

Specifically, in the strongly acidic environment, the polyaniline group of the NMPA-CS and NPA-CS are doped by the proton from the environment. Thus, the NMPA-CS and NPA-CS are in the doping form. In the neutral environment, the proton of the polyaniline in the NMPA-CS is stabilized by the ionisable, negatively charged functional group (MPS-Na) conjugated on polyaniline side chains of NMPA-CS. However, since the environment lacks protons and the NPA-CS does not have the negatively charged functional group, the NPA-CS is deprotonated. In other words, in contrast with the NPA-CS, NMPA-CS is in the doping form in different environment pH values.

Figure 3:
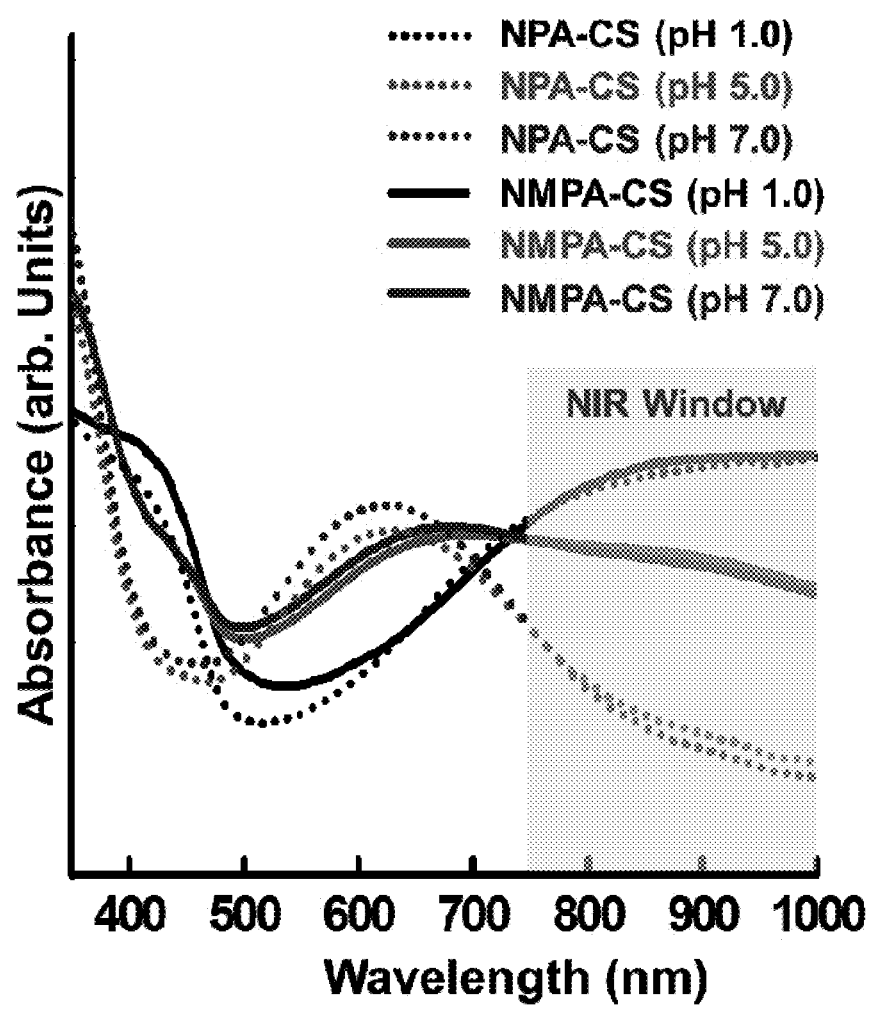
FIG. 3 shows the absorption spectra of NPA-CS and NMPA-CS in different pH environments in accordance with the embodiment of the instant disclosure.

FIG. 3 shows the absorption spectra of NPA-CS and NMPA-CS in different pH environments in accordance with the embodiment of the instant disclosure. As shown in FIG. 3, at the pH 7 environment, the NMPA-CS has an absorption in the NIR wavelength region range from 750 to 1000 nm Besides, the absorption of the NMPA-CS maintains in a certain value. On the other hand, at the pH 7 environment, the absorption of the NPA-CS in the NIR wavelength region is extremely decreased. In other word, in the physiologic environment, the polyaniline of the NMPA-CS is self-doped by its own MPS group, thus, the NMPA-CS has a much stronger absorption in the NIR wavelength region than NPA-CS. The photosensitivity of the NMPA-CS is better than the photosensitivity of the NPA-CS. The absorption of the NMPA-CS and the NPA-CS at pH 1.0 and pH 5.0 are also shown in FIG. 3.

Figure 4A:
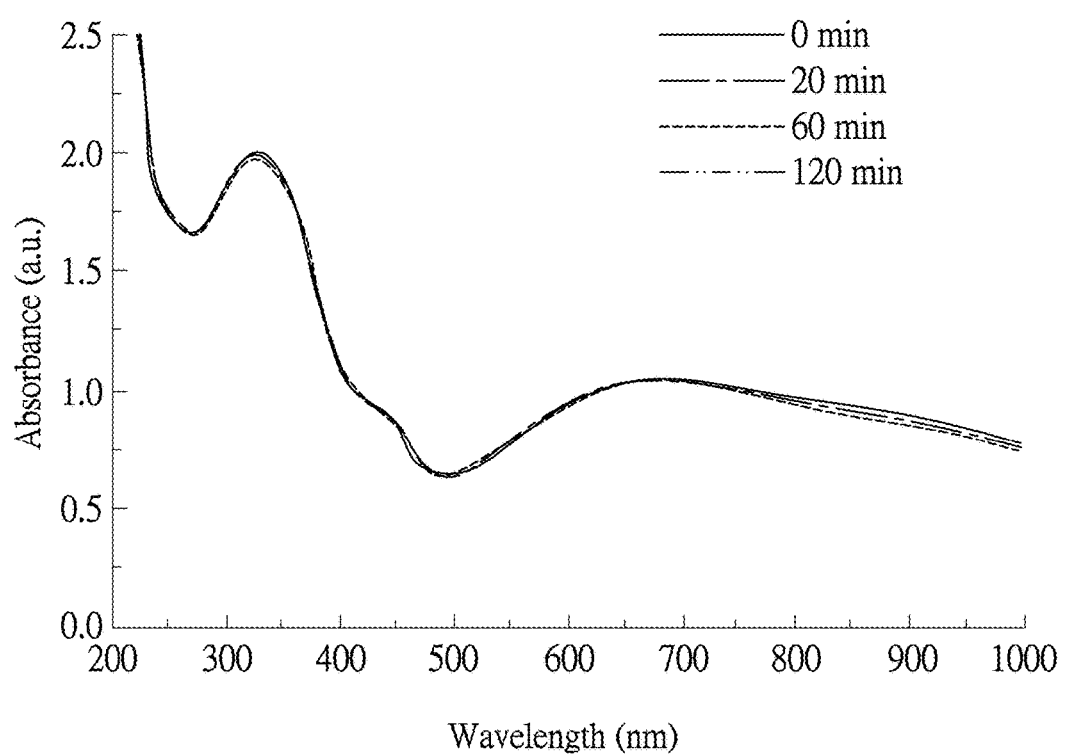
FIG. 4A shows the UV-vis absorption spectra of NMPA-CS aqueous solution under different irradiated times by NIR light in accordance with the embodiment of the instant disclosure.

In addition, the photostabilities of the NMPA-CS after irradiating for different time periods by NIR light are evaluated. In the present embodiment, the NMPA-CS converts the NIR light into heat energy after being exposed to the NIR light for 0 to 2 hours. FIG. 4A shows the UV-vis absorption spectra of NMPA-CS aqueous solutions under different irradiated times by NIR light in accordance with the embodiment of the instant disclosure. Specifically, the experiment result shown in FIG. 4A is the absorption changes of the NMPA-CS recorded after being illuminated by a high power laser for distinct periods of time. The experiment times include 0, 20, 60, and 120 minutes. The wavelength of the NIR light is 808 nm and the power of the NIR light is 4.0 W $cm^{-2}$. As shown in FIG. 4A, in the present embodiment, no matter how long the experiment times are, the absorption of the NMPA-CS is maintained in the range from 0.5 to 1 a.u. in the NIR wavelength region. In detail, the absorption of the NMPA-CS after being illuminated by the NIR light for 120 minutes is only decreased about 7 to 8% compared to being illuminated for 0 minutes. In other words, no significant absorption changes are observed during a long period of laser exposure. The photostability of the NMPA-CS is excellent.

Figure 4B:
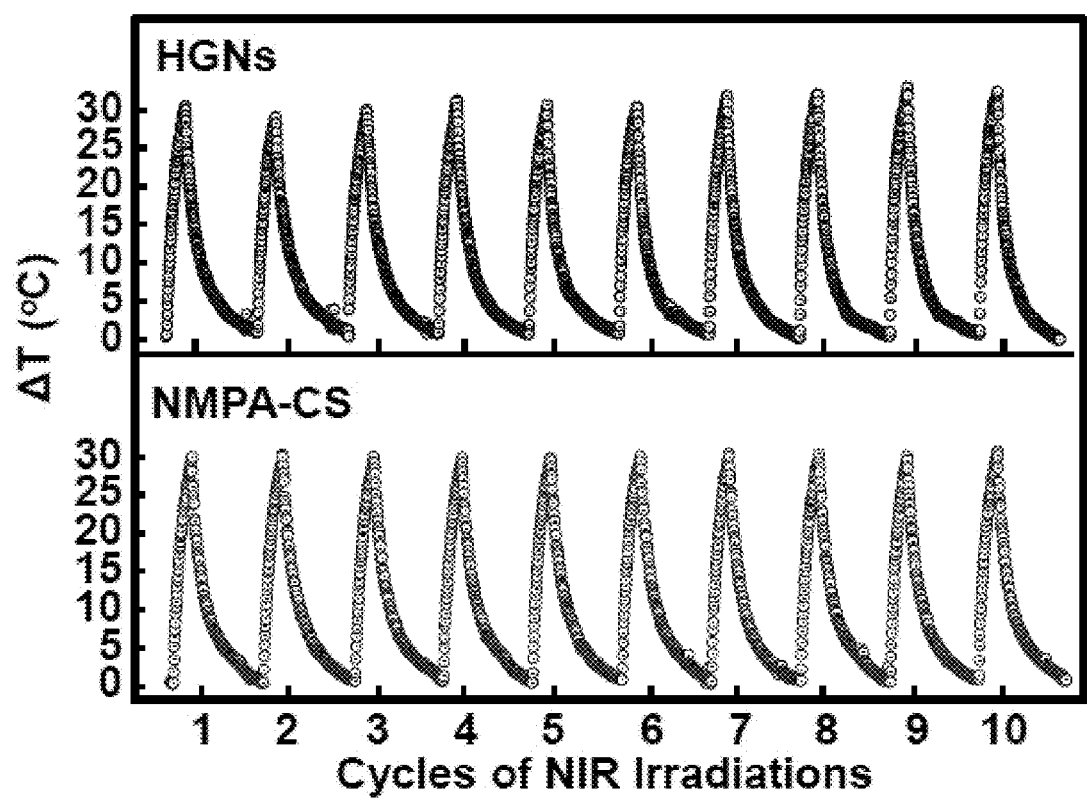
FIG. 4B shows the temperature evolution curves of the NMPA-CS and hollow gold nanosphere (HGN) under a plurality of irradiation circles in accordance with the embodiment of the instant disclosure.

Moreover, please refer to FIG. 4B. FIG. 4B shows the temperature evolution curves of the NMPA-CS and hollow gold nanosphere (HGN) under a plurality of irradiation circles in accordance with the embodiment of the instant disclosure. The hollow gold nanosphere is used as a comparative example regarding the NMPA-CS for evaluating the photostability of the NMPA-CS. As shown in FIG. 6B, after a plurality of circles of irradiation, the temperature evolution curves of the NMPA-CS remain substantially the same and hence, the NMPA-CS exhibits good photostability relative to the HGN.

Figure 5:
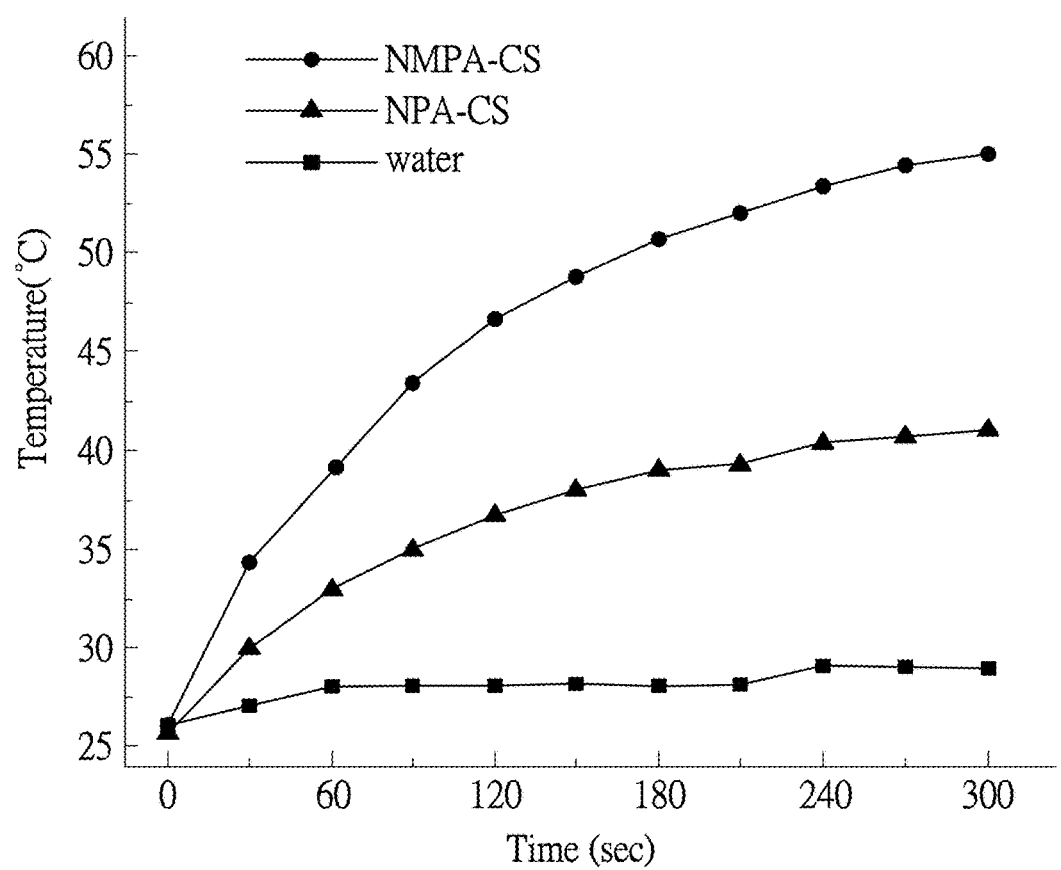
FIG. 5 shows the temperature evolution curves of NMPA-CS and NPA-CS under NIR light irradiation in accordance with the embodiment of the instant disclosure.

Next, the photo-thermal conversion efficiencies of the NMPA-CS and the NPA-CS are evaluated. FIG. 5 shows temperature evolution curves of NMPA-CS and NPA-CS under NIR light irradiation in accordance with the embodiment of the instant disclosure. Specifically, the experiment result shown in FIG. 5 is the temperature changes of the NMPA-CS and the NPA-CS recorded after being illuminated by NIR light for distinct periods of time. As shown in FIG. 5, the temperature of the NPA-CS increases from 30° C. to 40° C., after being exposed to the NIR light for 300 seconds. However, the temperature of the NMPA-CS achieves 50° C.

after being exposed to the NIR light for only 150 seconds. In other words, the photo-thermal conversion efficiency of the NMPA-CS is better than the efficiency of the NPA-CS. As explained in the description of related art, the temperature higher than 50° C. causes the damage and the death of the bacteria and tumor tissues. As the result shown in FIG. 5, after being exposed to the NIR light, the temperature of the NMPA-CS is equal to or even higher than 50° C. Thus, while the NMPA-CS is injected into the infection potion/tumor tissue and is exposed to the NIR light, the bacteria/cancer cells inside the infection portion can be killed.

Figure 6:
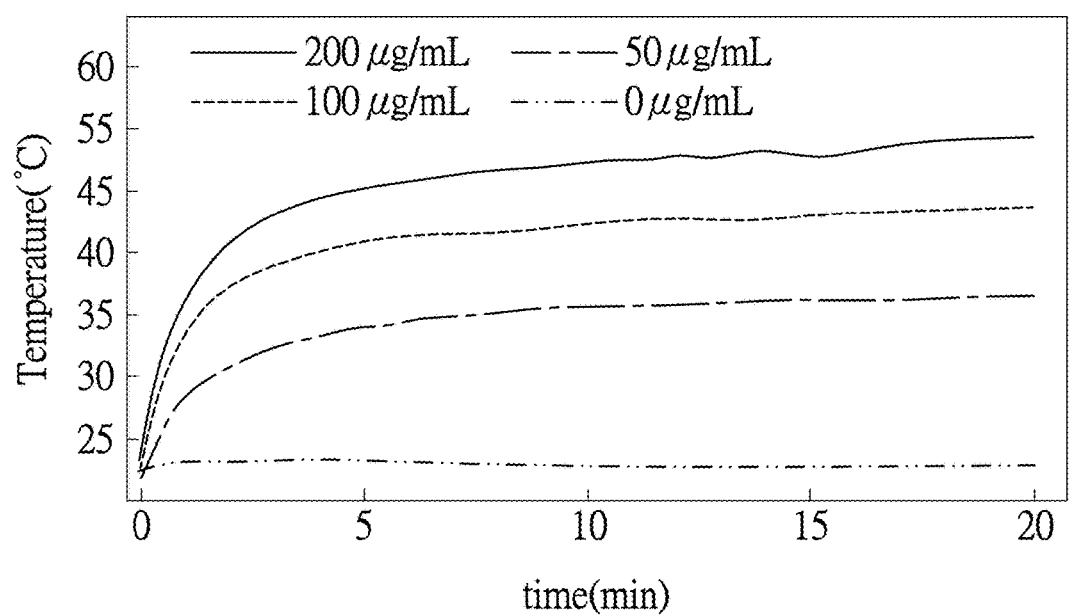
FIG. 6 shows the temperature evolution curves of the ager-gels containing different concentration of NMPA-CS under NIR light irradiation in accordance with the embodiment of the instant disclosure.

FIG. 6 shows the temperature evolution curves of the ager-gels containing different concentrations of NMPA-CS under NIR light irradiation in accordance with the embodiment of the instant disclosure. In the present embodiment, aqueous NMPA-CS at different concentrations, 0 μg/ml, 50 μg/ml, 100 μg/ml, and 200 μg/ml, is mixed with Mueller-Hinton agar and allowed to complete gelation. Then, the agar-gels containing different concentrations of NMPA-CS are individually exposed to an 808 nm NIR light (2.0 W cm$^{-2}$). The temperature profiles are collected for distinct periods of times. As shown in FIG. 6, after illuminating by the NIR light for 1 minute, the temperatures of the agar-gels containing the NMPA-CS at 50 μg/ml, 100 μg/ml, and 200 μg/ml are elevated to 35, 40, and 45° C. individually. In fact, the heating rate of the agar-gels containing the 200 μg/ml of the NMPA-CS is better than the other concentrations, the temperature of which elevated to 45° C. within 1 minute. In addition, as shown in FIG. 6, the temperature of the agar-gels containing the 200 μg/ml of the NMPA-CS elevated to 55° C. within 20 minutes. It worth noting that, the magnitude of temperature elevated is dependent upon the concentration of the NMPA-CS and the exposing time of the NIR light. In reality, the temperature can be elevated to the range between 35 to 80° C.

The photo-thermal therapy is used to treat the subcutaneous tissue disease or skin disease caused by bacteria. In the present embodiment, the subcutaneous abscess is taken as an example to describe the bactericidal effect of the NMPA-CS in photo-thermal therapy. Recently, the methicillin-resistant *staphylococcus aureus* (MRSA) has become a common cause, presenting as more complicated forms of subcutaneous infections.

Figure 7A:
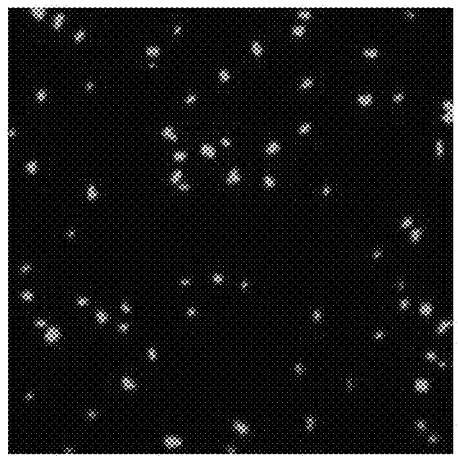
FIG. 7A to 7D are the Live and Dead staining images of bacteria after receiving different treatment in accordance with the embodiment of the instant disclosure.
Figure 7B:
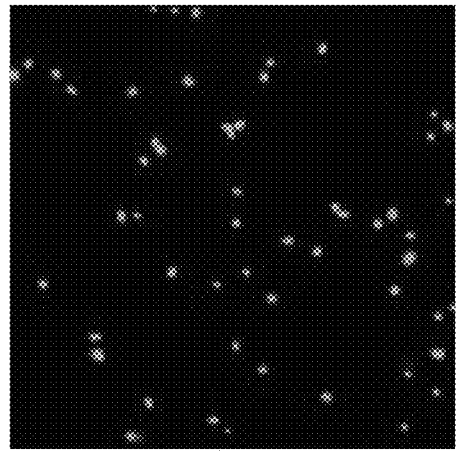
Figure 7C:
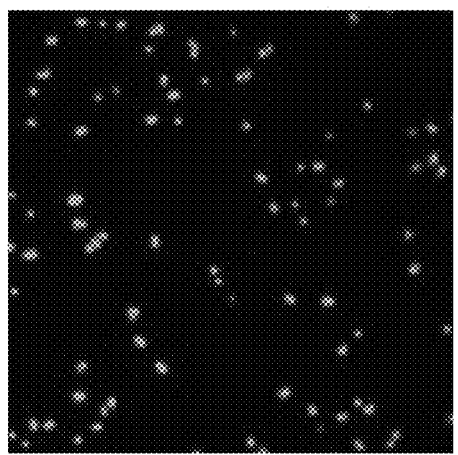
Figure 7D:
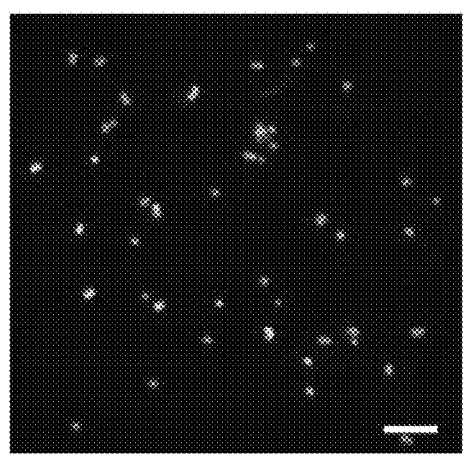

FIG. 7A to 7D are the Live and Dead staining images of bacteria (MRSA) that have received different treatments in accordance with the embodiment of the instant disclosure. FIG. 7A is the Live and Dead staining image of the MRSA without any treatment. FIG. 7B is the Live and Dead staining image of the MRSA exposed to the 808 nm NIR light alone. FIG. 7C is the Live and Dead staining image of MRSA treated with the NMPA-CS only. In FIG. 7C, MRSA is suspended in an aqueous solution containing NMPA-CS at a concentration of 200 μg/mL FIG. 7D is the Live and Dead staining image of the MRSA treated with the NMPA-CS at a concentration of 200 μg/mL and irradiated by the 808 nm NIR light. It worth noting that, in FIG. 7A to 7D, at 20 minutes after each treatment, test MRSA are collected by centrifugation, and their viability are evaluated by using the LIVE/DEAD BacLight Bacterial Viability Kit. With this specific kit, live bacteria with intact cell membranes stain fluorescent green, whereas dead bacteria with damaged membranes stain fluorescent red.

Comparing FIGS. 7A and 7B, the test MRSA in the FIG. 7B mainly emits green fluoresce. Greater than 96% of MRSA are still alive. In other words, the treatment with NIR light alone produces insignificant effects on the viability of bacteria. Comparing FIGS. 7A and 7C, greater than 96% of the MRSA are still alive. In other words, the treatment with NMPA-CS alone also produces insignificant effect on the viability of bacteria. However, compare FIGS. 7A and 7D, while the MRSA is suspended in the NMPA-CS solution and is exposed to the NIR light, there is a markedly increment in the number of dead or compromised cells, as indicated by the prevalence of dead cells. Less than 6% of the MRSA are alive.

As shown in FIG. 6A, the temperature of the NMPA-CS solution indeed increases after exposing to the NIR light. It worth noting that, while the temperature is greater than 50° C., the enzymes within bacteria are denatured and their proteins and lipids on the cell membranes are damaged, and this eventually leads to bacterial death. Thus, in view of the description of FIG. 7D, while the temperature of the NMPA-CS is elevated to 50° C., the bacteria suspend in the NMPA-CS solution is dead.

Figure 8A:
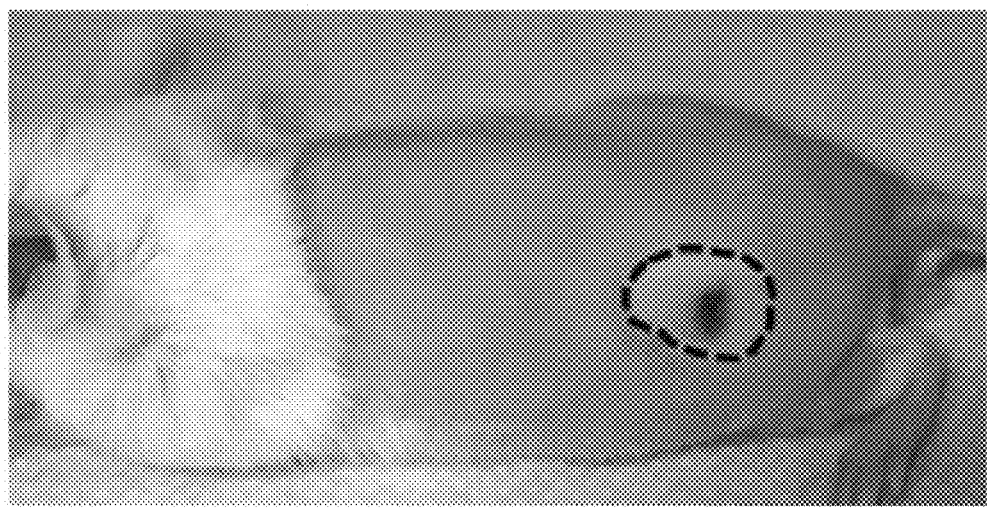
FIG. 8A is a photograph of a mouse injected with NMPA-CS at the site of infection and then irradiated by NIR light in accordance with the embodiment of the instant disclosure.
Figure 8B:
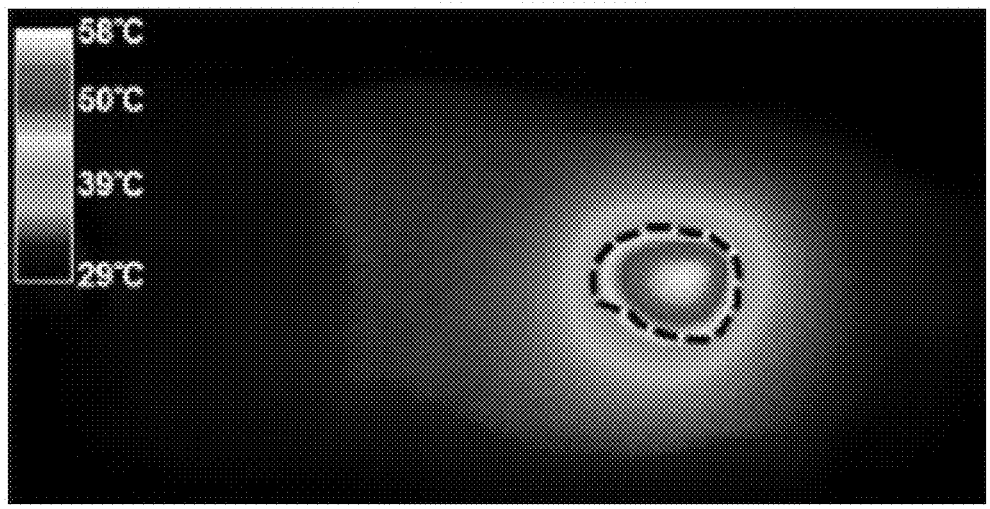
FIG. 8B is a thermographic image of the mouse injected with NMPA-CS at the site of infection and then irradiated by NIR light in accordance with the embodiment of the instant disclosure.

Furthermore, in the present embodiment, the efficacy of the NMPA-CS as a photo-thermal agent locally in vivo is tested. FIG. 8A is a photograph of mouse injected with the NMPA-CS at the site of infection and then irradiated by NIR light in accordance with the embodiment of the instant disclosure. FIG. 8B is a thermographic image of the mouse injected with NMPA-CS at the site of infection and then irradiated by the NIR light in accordance with the embodiment of the instant disclosure. Specifically, in the experiment of FIGS. 8A and 8B, a mouse model with a subcutaneous abscess is experimentally created via local injection 100 μL of the MRSA. The concentration of the MRSA is $10^7$ CFU/mL After 24 hours, an infected wound is formed subcutaneously. Then, 100 μL of a viscous NMPA-CS solution is injected at the site of the infection through a 25G needle. The concentration of the NMPA-CS solution is 30 mg/mL and the pH value of the solution is 6.3.

It worth noting that, the pH value inside the organism is 7.4 and the pH value of the subcutaneous abscess is in the range from 6.0 to 6.6. Since the chitosan group of the NMPA-CS is a pH-responsive hydrogelation, while the NMPA-CS solution is injected into the infection site, the NMPA-CS is spread over the acidic area of abscesses (pH value is in the range from 6.0 to 6.6). However, the NMPA-CS is transformed into hydrogels once the NMPA-CS is spread onto the healthy tissues (pH value is in the range from 7.0 to 7.4). Thus, the NMPA-CS hydrogel is immobilized in the infection site. Then, the infection site is exposed to the NIR light. In the present embodiment, the wavelength of the NIR light is 808 nm, and the power of the NIR light is 0.5 W cm$^{-2}$.

FIG. 8A is the photograph of mouse after both of the MRSA and the NMPA-CS are injected into the mouse. FIG. 8B is the thermographic image of the mouse after irradiating by the NIR light. As shown in FIG. 8B, after exposing to the NIR light, the temperature of the infection site injected with the NMPA-CS is elevated to the range from 50° C. to 55° C. The temperature of the NMPA-CS higher than 50° C. causes the damage and the death of the bacteria, thus the NMPA-CS indeed has the bactericidal effect. In addition, FIG. 8B also shows that the NMPA can inject into the specific region of the organism by injection. According to FIG. 8B, only the region with the con-existence of NMPA-CS and NIR light exhibited a sharp rise in temperature. No significant temperature change is observed on other parts of the mouse. In other words, in reality, the user can inject the NMPA-CS into a specific infection site and then irradiate the NMPA-CS by the NIR light without damaging the surrounding tissues.

Figure 9:
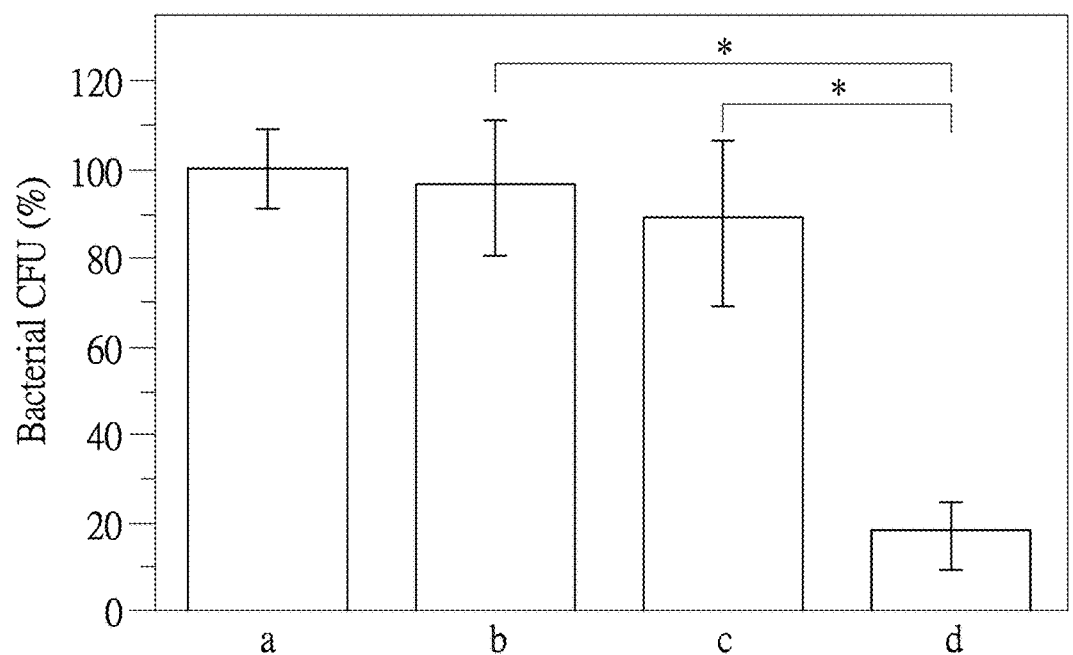
FIG. 9 is a schematic view of the quantified result of bacteria obtained from the infected tissue of a mouse treated with different experimental conditions in accordance with the embodiment of the instant disclosure.

FIG. 9 is a schematic view of the quantified result of bacteria obtained from the infected tissue of mice treated with different experimental conditions in accordance with the embodiment of the instant disclosure. In the experiment of FIG. 9, $10^7$ CFU/mL and 100 μL of the MRSA is injected into 6 mice. 24 hours later, an infected wound is formed subcutaneously. In FIG. 9, "a" represents the bacterial quantity of the infected wound without any treatment, "b" represents the bacterial quantity of the infected wound after exposing to the 808 nm NIR light for 20 minutes only, "c" represents the bacterial quantity of the infected wound injected with the 30 μg/mL of NMPA-CS hydrogel, and "d" represents the bacterial quantity of the infected wound treated with the 30 μg/mL of NMPA-CS hydrogels and exposed to the 808 nm NIR light for 20 minutes.

As shown in FIG. 9, the bacterial quantity of the infected wound after exposing to the NIR light is higher than 95%. The bacterial quantity of the infected wound injected with the 30 μg/mL of NMPA-CS hydrogel is higher than 90%. In other words, the treatment with the NIR light alone or the NMPA-CS alone produces insignificant effect on the death of the bacteria. However, the bacterial quantity of the infected wound injected with NMPA-CS hydrogel is less than 20% after exposing to the NIR light. In other words, after exposing to the NIR light, the temperature of the NMPA-CS is increased. Thus, a large number of the bacteria inside the infection site are killed. The result of the in vivo test in FIG. 9 is similar to the in vitro test in FIG. 7A to 7D.

Figure 10A:
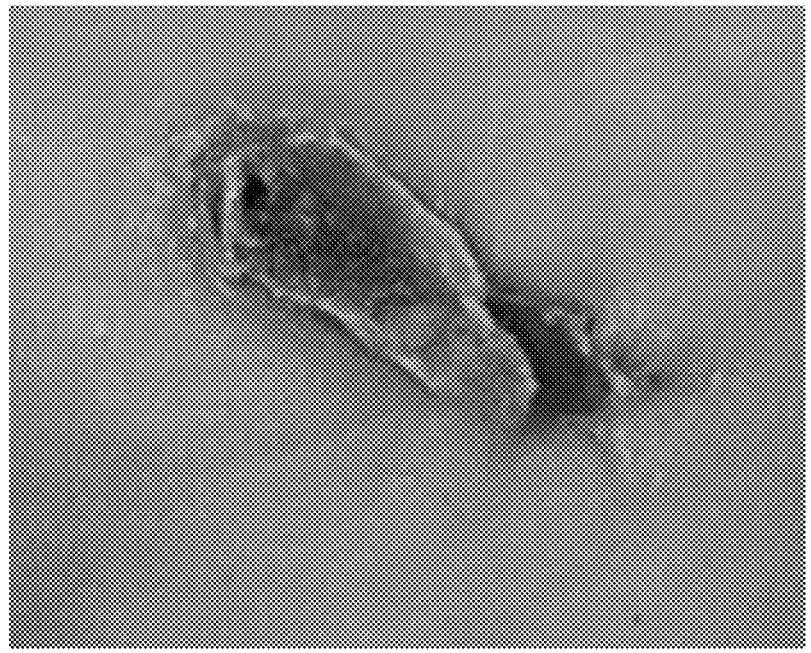
FIGS. 10A and 10B are the photographs of the infected skin of the mice with NMPA-CS and laser treatment on different treating days in accordance with the embodiment of the instant disclosure.
Figure 10B:
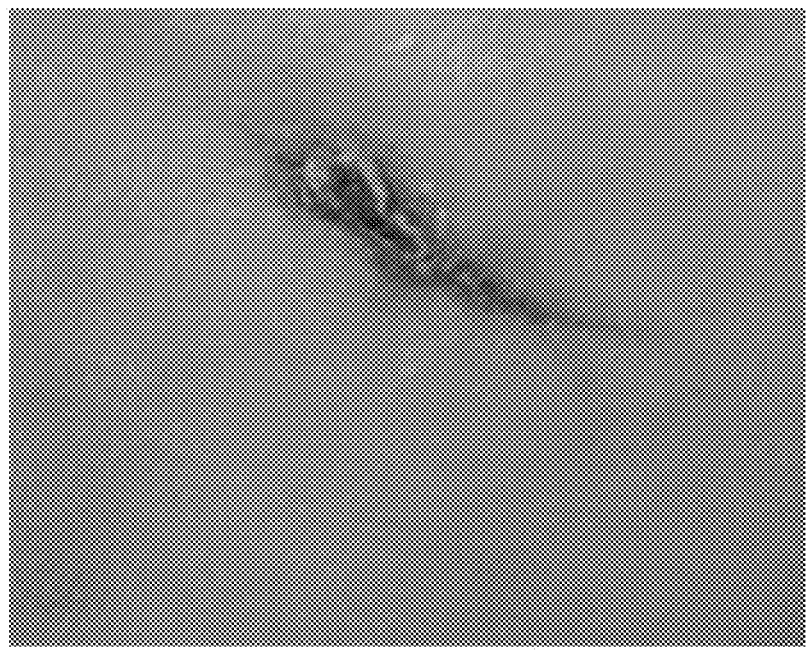

FIGS. 10A and 10B are the photographs of the infected skin of the mouse with the NMPA-CS and the laser treatment in different treating days in accordance with the embodiment of the instant disclosure. FIG. 10A is the photograph of the infection skin of a mouse after NMPA-CS and NIR light treatment for 7 days. FIG. 10B is the photograph of the infection skin of a mouse after NMPA-CS and NIR light treatment for 10 days. The lump in FIG. 10A is a scab resulting from the biological process of wound repair. The black portion shown in the middle of the scab is the NMPA-CS. In addition, as shown in FIG. 10B, the scab together with the implanted NMPA-CS hydrogels flaked off within 10 days. In other words, after the photo-thermal treatment, the NMPA-CS does not remain inside the organism.

Figure 11C:
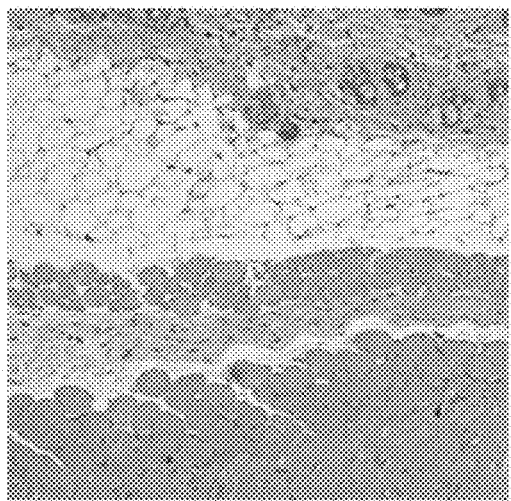
Figure 11C:
Figure 11C:
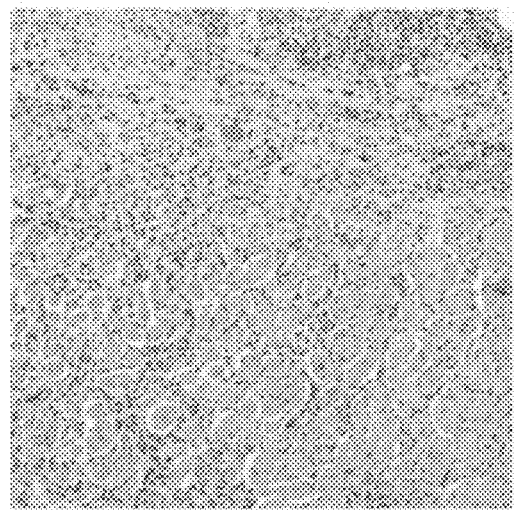

FIG. 11A to 11C are the Histological H&E stain photomicrographs of the skin tissue section of infected mice before and after the NMPA-CS and the laser treatment in accordance with the embodiment of the instant disclosure. FIG. 11A is the Histological H&E stain photomicrograph of the health skin tissue. FIG. 11B is the Histological H&E stain photomicrograph of the infected skin tissue before the NMPA-CS and the NIR treatment. FIG. 11C is the Histological H&E stain photomicrograph of the infected skin tissue after NMPA-CS and NIR treatment. Comparing FIGS. 11A and 11B, signs of severe infection are noticed before treatment. In contrast, comparing FIGS. 11A and 11C, the architecture of the skin tissues is found to be repaired, implying the highly bactericidal effect of the photo-thermal treatment by the NMPA-CS.

It worth noting that, in the present embodiment, the NMPA-CS is not limited to treat the subcutaneous tissue disease caused by MRSA. The temperature of the NMPA-CS is elevated to the range from 35 to 80° C. Thus, the (acid-substituted polyaniline)-grafted hydrogel copolymer can be used as the photo-thermal agent of the photo-thermal therapy to treat the disease caused by the bacteria which can be damaged or killed in the condition of high temperature.

Figure 12A:
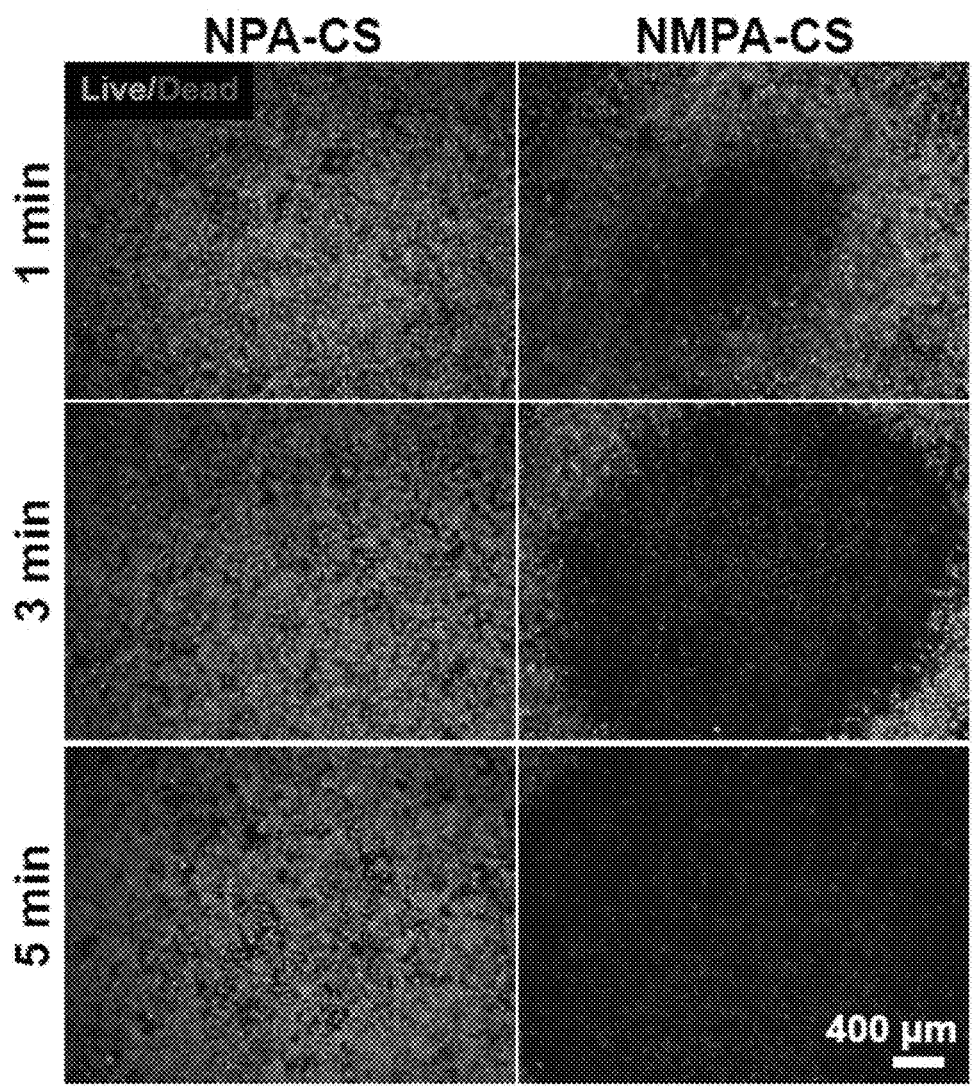
FIG. 12A shows the Live and Dead staining images of tumor cells after receiving different treatments in accordance with the embodiment of the instant disclosure.
Figure 12B:
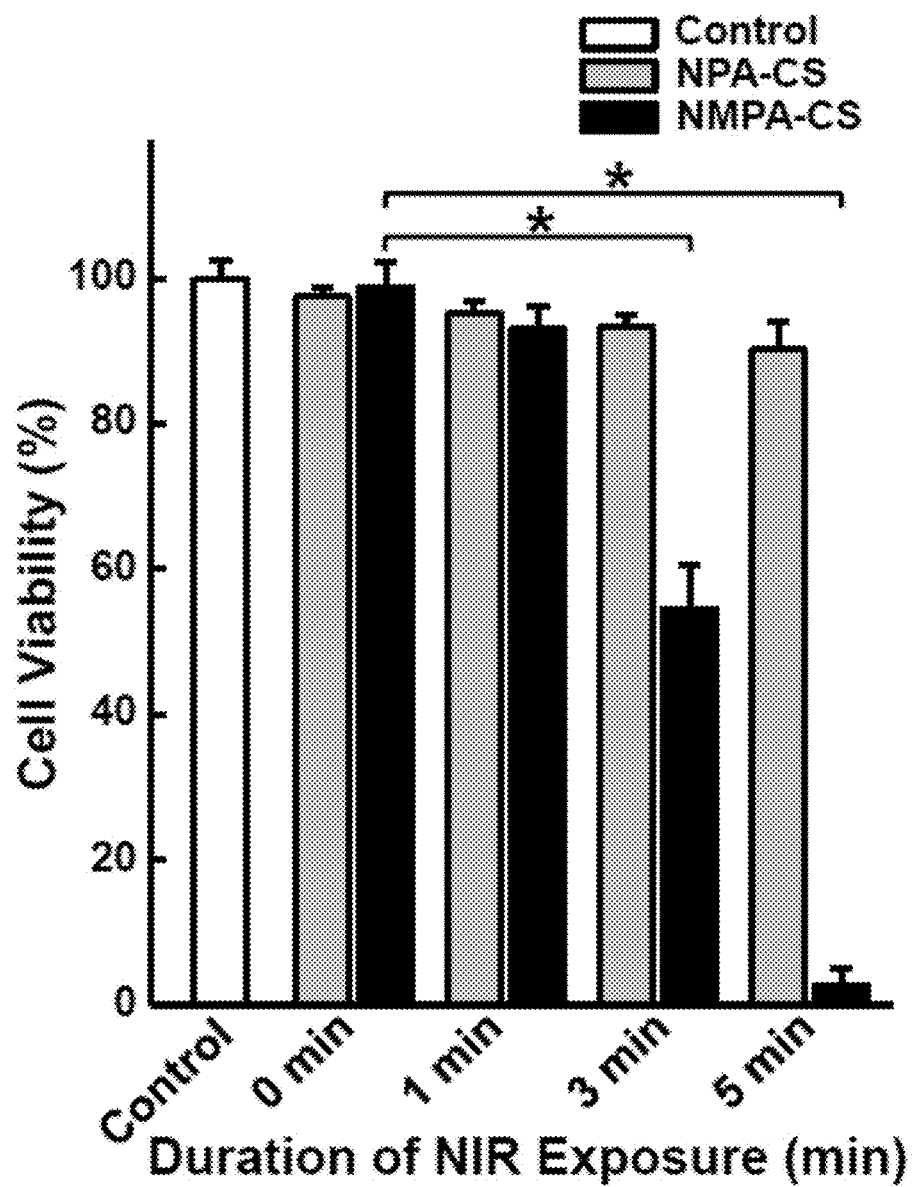
FIG. 12B shows the results of the viability test of the tumor cells after receiving different treatments in accordance with the embodiment of the instant disclosure.

In another embodiment of the instant disclosure, the (acid-substituted polyaniline)-grafted hydrogel copolymer is used as a photo-thermal agent for treating cancer cells. In the present embodiment, NPA-CS and HGNs are used as comparative examples. FIG. 12A shows the Live and Dead staining images of tumor cells after receiving different treatments (using NPA-CS and NMPA-CS respectively), and FIG. 12B shows the results of the viability test of the tumor cells. As shown in FIG. 12A and FIG. 12B, comparing to the cell viability after treating the cancer cells by the NPA-CS and exposed to an NIR laser (2 W/cm$^2$), the viability of the cancer cells significantly decreases after treating the cancer cells by the NMPA-CS and exposed to an NIR laser (2 W/cm$^2$) for 5 minutes.

Figure 13:
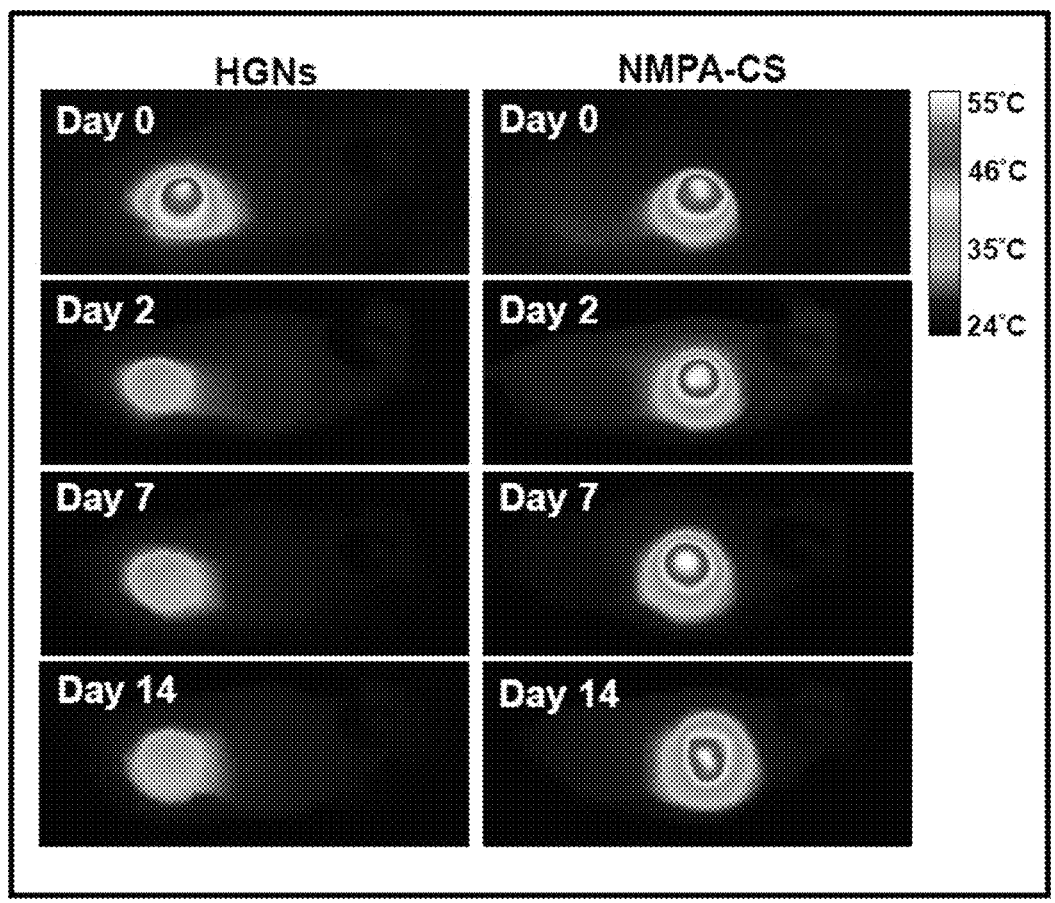
FIG. 13 is a thermographic image of a mice injected with HGNs and NMPA-CS at the site of the tumor and then irradiated by NIR light in accordance with the embodiment of the instant disclosure.

FIG. 13 is a thermographic image of a mice injected with HGNs and NMPA-CS at the site of the tumor and then irradiated by NIR light. Based on the property of forming hydrogels after being injected into living bodies, NMPA-CS can stay for longer time inside the mouse. As shown in FIG. 13, the NMPA-CS stays in the mouse for at least 14 days. In contrast thereto, HGNs shows no thermal signals above 40° C. after only 2 days.

Figure 14A:
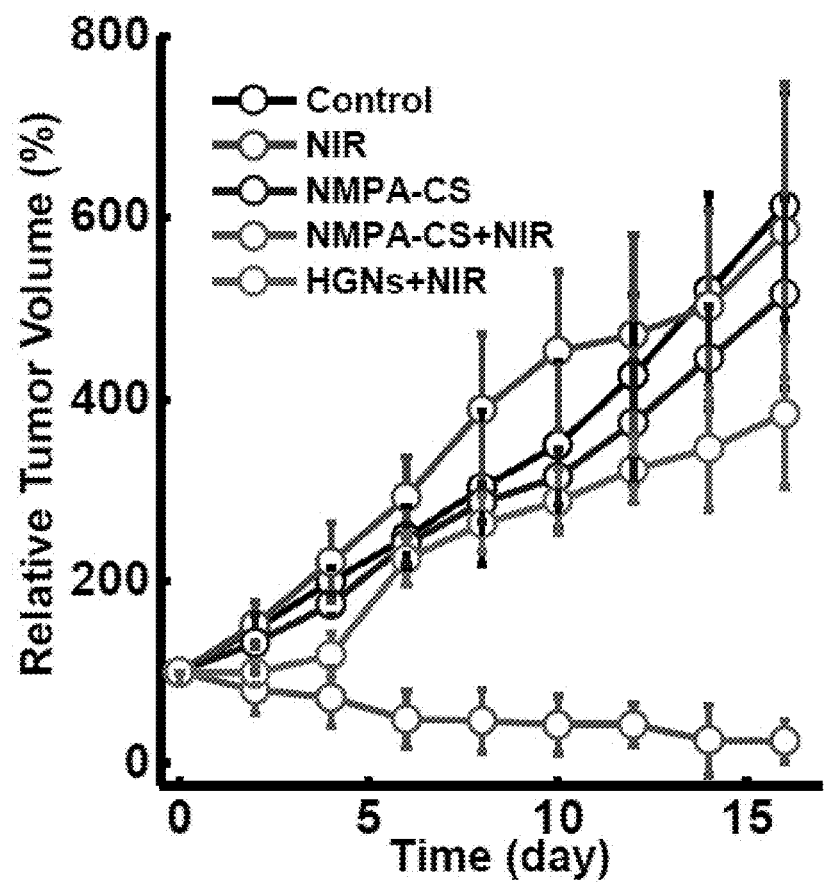
FIGS. 14A and 14B show the quantified results of photo-thermal therapy including the relative tumor volume and body weight of the mouse in accordance with the embodiment of the instant disclosure.
Figure 14B:
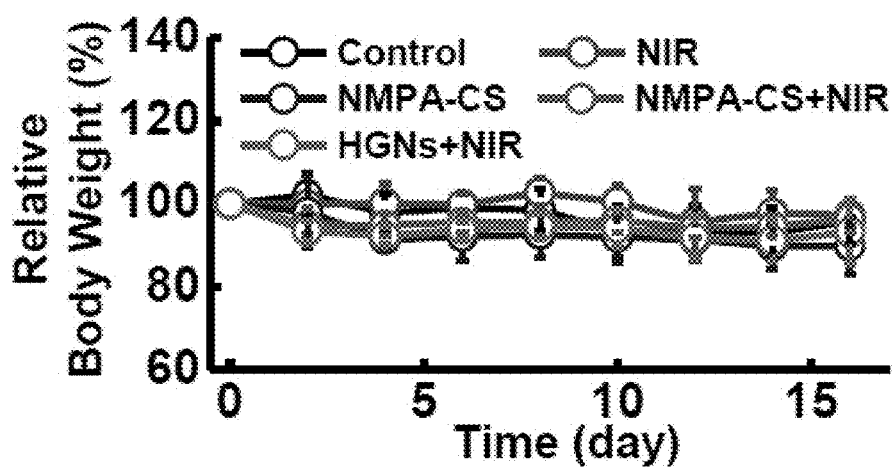
Figure 15:
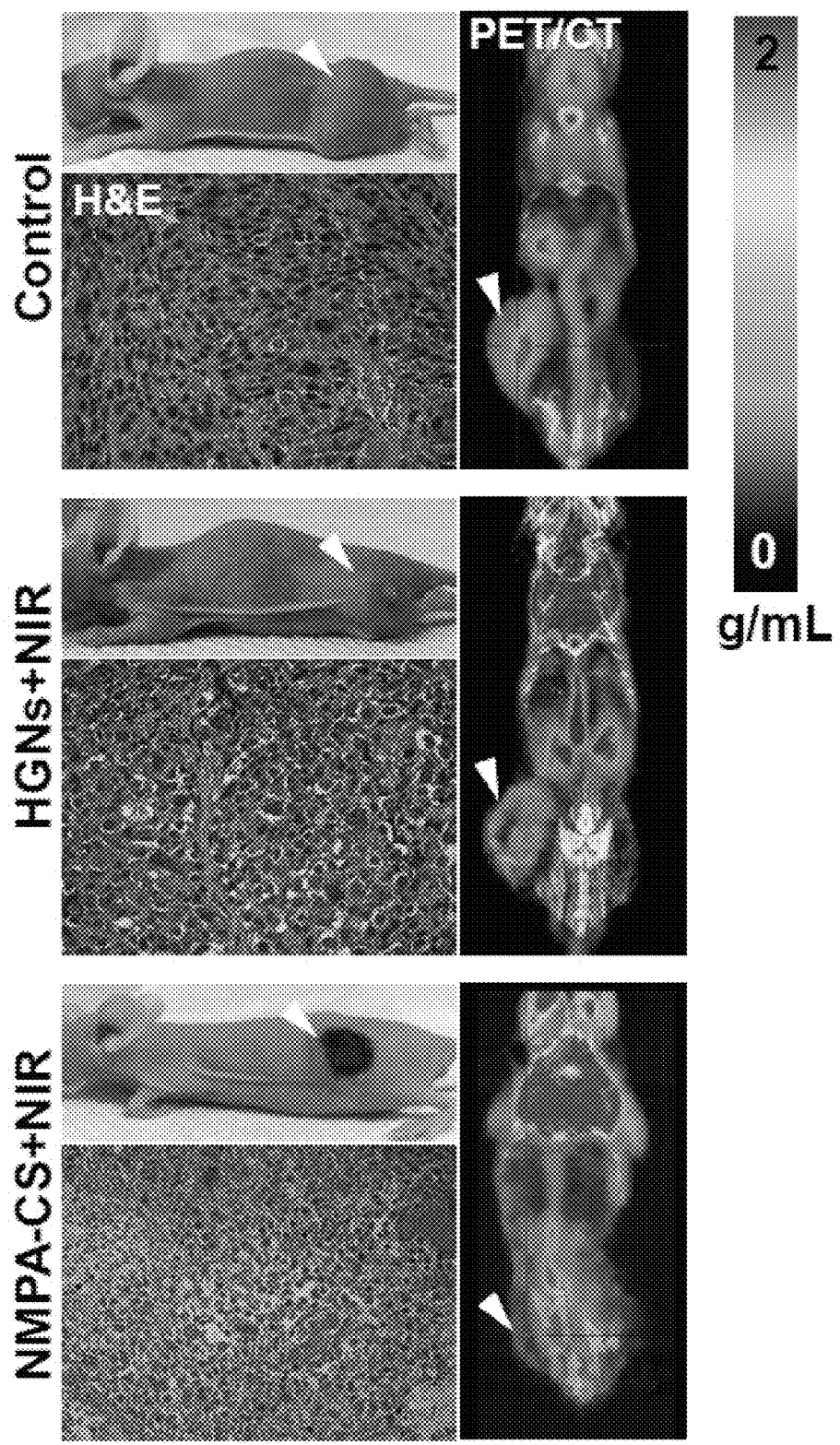
FIG. 15 shows the photographs of photo-thermal therapy including the appearance, PET photographs and H&E stain result in accordance with the embodiment of the instant disclosure.

FIGS. 14A and 14B show the quantified results of photo-thermal therapy including the relative tumor volume and body weight of the mouse and FIG. 15 shows the photographs of photo-thermal therapy including the appearance, PET photographs and H&E stain result. As shown in FIG. 14A, the relative tumor volume decrease significantly while using NMPA-CS as the photo-thermal agent. FIG. 15 shows the comparison between using NMPA-CS as photo-thermal agent and using HGNs as photo-thermal agent, and the results shows that NMPA-CS has high efficiency for treating cancer cells.

In summary, the instant disclosure provides the (acid-substituted polyaniline)-grafted hydrogel copolymer. The hydrogel copolymer is formed by the polymerization and substitution reaction between chitosan, polyaniline, and proton acid. The chitosan group makes the hydrogel copolymer be transformed into hydrogels in a process that is driven by a local change in pH. The polyaniline group grafted by the acid proton group makes the hydrogel copolymer have an absorption in the NIR wavelength region. The proton acid group makes the polyaniline group maintain in the doped form.

The figures and descriptions supra set forth illustrated the preferred embodiments of the instant disclosure; however, the characteristics of the instant disclosure are by no means restricted thereto. All changes, alterations, combinations or modifications conveniently considered by those skilled in the art are deemed to be encompassed within the scope of the instant disclosure delineated by the following claims.

What is claimed is:

1. A method of treating a bacterial infection comprising sequentially performing following steps:
    a) injecting a photo-thermal agent having the general formula shown as below at an infection site that is caused by bacteria, the photo-thermal agent is formed from a chitosan group, a polyaniline group, and a proton acid group by a polymerization process:

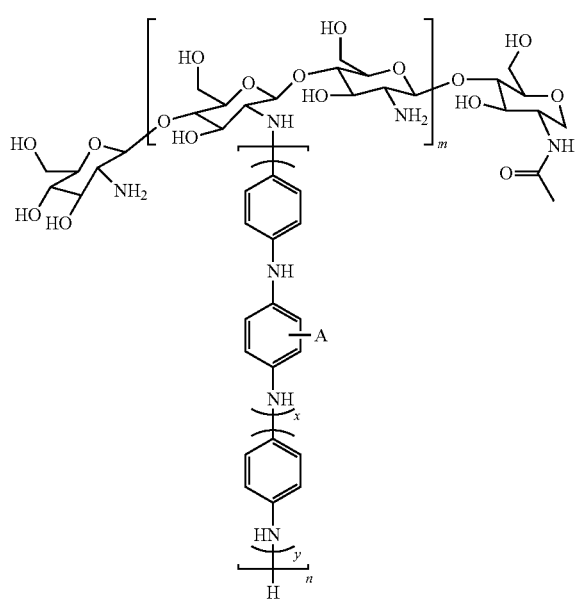

wherein A is a proton acid group, m and n are same or different integers greater than 0, x is an integer equal to or greater than 0, and y is an integer equal to or greater than 1, provided that x and y are the same or different at each occurrence, and at least an x is not 0;

wherein the proton acid group is selected from the group consisting of: 3-mercapto-1-propanesulfonic acid sodium salt (MPS-Na), 3-mercaropropinoic acid, and thioglycolic acid; and b) exposing the infection site to Near-Infrared light for generating a heat energy to kill the bacteria inside the infection site.

2. The method of claim 1, wherein the polymerization process comprises a first step for grafting the polyaniline group on the chitosan group and a second step for grafting the proton acid group on the polyaniline group, wherein a polymerization time of the first step is in the range of 3.5 to 4.5 hours, and a polymerization time of the second step is in the range of 12 to 16 hours.

3. The method of claim 1, wherein when the (acid-substituted polyaniline)-grafted hydrogel copolymer is exposed to a near-infrared light, the temperature of the (acid-substituted polyaniline)-grafted hydrogel copolymer is in the range of 35 to 80° C.

4. The method of claim 1, wherein after the (acid-substituted polyaniline)-grafted hydrogel copolymer is exposed to a near-infrared light for 1 minute to 4 hours, the (acid-substituted polyaniline)-grafted hydrogel copolymer converts the near-infrared light into a heat energy.

5. The method of claim 1, wherein when the (acid-substituted polyaniline)-grafted hydrogel copolymer is in an environment at pH between 1 to 8, the (acid-substituted polyaniline)-grafted hydrogel copolymer has an absorption in the NIR wavelength region.

6. The method of claim 1, wherein the wavelength of the Near-Infrared light is from 750 to 1000 nm.

7. The method of claim 1, wherein the photo-thermal therapy is a therapy used to treat a disease caused by a bacteria.

8. A method of treating a cancerous tumor comprising sequentially performing following steps:

a) injecting a photo-thermal agent having the general formula shown as below at a tumor tissue that is formed by cancer cells, the photo-thermal agent is formed from a chitosan group, a polyaniline group, and a proton acid group by a polymerization process:

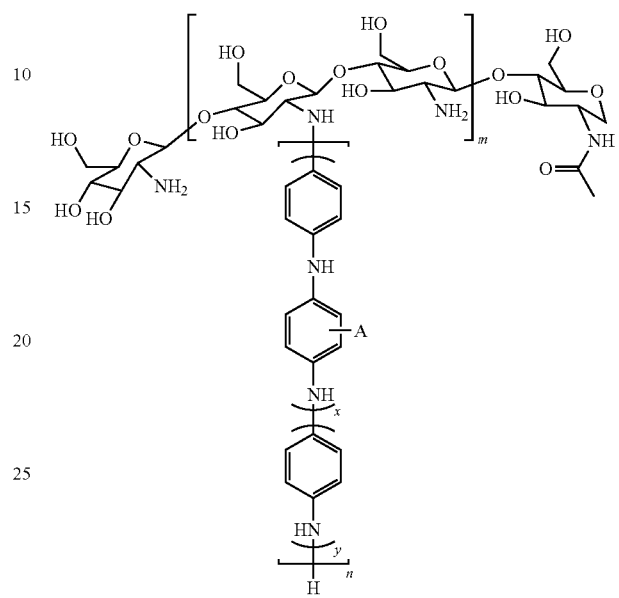

wherein A is a proton acid group, m and n are same or different integers greater than 0, x is an integer equal to or greater than 0, and y is an integer equal to or greater than 1, provided that x and y are the same or different at each occurrence, and at least an x is not 0;

wherein the proton acid group is selected from the group consisting of: 3-mercapto-1-propanesulfonic acid sodium salt (MPS-Na), 3-mercaropropinoic acid, and thioglycolic acid; and b) exposing the tumor tissue to Near-Infrared light for generating a heat energy to kill the cancer cells in the tumor tissue.

9. The method of claim 8, wherein the polymerization process comprises a first step for grafting the polyaniline group on the chitosan group and a second step for grafting the proton acid group on the polyaniline group, wherein a polymerization time of the first step is in the range of 3.5 to 4.5 hours, and a polymerization time of the second step is in the range of 12 to 16 hours.

10. The method of claim 8, wherein when the (acid-substituted polyaniline)-grafted hydrogel copolymer is exposed to a near-infrared light, the temperature of the (acid-substituted polyaniline)-grafted hydrogel copolymer is in the range of 35 to 80° C.

11. The method of claim 8, wherein after the (acid-substituted polyaniline)-grafted hydrogel copolymer is exposed to a near-infrared light for 1 minute to 4 hours, the (acid-substituted polyaniline)-grafted hydrogel copolymer converts the near-infrared light into a heat energy.

12. The method of claim 8, wherein when the (acid-substituted polyaniline)-grafted hydrogel copolymer is in an environment at pH between 1 to 8, the (acid-substituted polyaniline)-grafted hydrogel copolymer has an absorption in the NIR wavelength region.

13. The method of claim 8, wherein the wavelength of the Near-Infrared light is from 750 to 1000 nm.

14. The method of claim 8, wherein the photo-thermal therapy is a therapy used to treat a disease caused by cancer cells.

\* \* \* \* \*